US006002986A

United States Patent [19]
Mito

[11] Patent Number: 6,002,986
[45] Date of Patent: Dec. 14, 1999

[54] FRACTION PURITY MEASURING APPARATUS FOR CHROMATOGRAM PEAK

[75] Inventor: Yasuhiro Mito, Umekohji-honmachi, Japan

[73] Assignee: Shimadzu Corporation, Japan

[21] Appl. No.: 07/792,404

[22] Filed: Nov. 15, 1991

[30] Foreign Application Priority Data

Nov. 16, 1990 [JP] Japan ................................ 2-312420
Apr. 25, 1991 [JP] Japan ................................ 3-124682

[51] Int. Cl.$^6$ .......................... B01D 15/08; G01N 21/00
[52] U.S. Cl. ........................................... 702/32; 702/23
[58] Field of Search ................................ 364/496–499;
702/32, 22, 23; 73/19.02, 19.1, 23.22, 23.36,
23.35, 61.52, 61.55; 210/656; 422/70, 89;
436/161

[56] References Cited

U.S. PATENT DOCUMENTS

| 3,504,174 | 3/1970 | Nisiwaki et al. ........................ 250/283 |
| 4,367,041 | 1/1983 | Webb, Jr. et al. ........................ 356/72 |
| 4,482,966 | 11/1984 | Mito et al. ............................... 364/418 |
| 4,760,331 | 7/1988 | Komuro et al. ...................... 324/121 R |
| 4,766,551 | 8/1988 | Begley .................................... 364/498 |
| 4,835,708 | 5/1989 | Frans ...................................... 364/497 |
| 5,175,430 | 12/1992 | Enke et al. ............................... 250/282 |

FOREIGN PATENT DOCUMENTS 2253155 of 0000 Japan .
2253156 of 0000 Japan .

OTHER PUBLICATIONS

Publication—Quantitative Resolution of Fused Chromatographic Peaks in Gas Chromatography/Mass Spectrometry, Muhammad Abdallah Sharaf et al., Anal. Chem. 1982.

Publication—Use of Multivariate Curve Resolution and a High–Speed Diode Array Ultraviolet Detector in Size–Exclusion Chromatography of Lignin–Based Copolymers, John C. Nicholson et al., Anal. Chem. 1984.

Zech, Karl and Reinhard Huber, "On–Line Screening for Drug Metabolites by High Performance Liquid Chromatography with a Diode Array UV Detector", Journal of Chromatography, 282 pp. 161–167, 1983.

Marr, J.G.D et al., "Multiple Absorbance Ratio Correlation—A New Approach for Assessing Peak Purity in Liquid Chromatography" Journal of Chromatography, 506 pp. 289–301, May 1990.

Yost, Roy, Stoveken, John and William MacLean, "Positive Peak Identification in Liquid Chromatography Using Absorbance Ratioing with a Variable–Wavelength Spectrophotometric Detector", Journal of Chromatography, 134, pp. 73–82, 1177.

*Primary Examiner*—Melanie A. Kemper
*Attorney, Agent, or Firm*—Klima & Hopkins, P.C.

[57] ABSTRACT

A detection signal from a multi-wavelength detector provided in a liquid chromatograph is stored in a data storage part, and a chromatogram is formed from the stored data with respect to a specific wavelength, to detect a peak from the chromatogram. The spectrum at a top of the peak to be identified or a known spectrum of a component to be identified is used as a reference spectrum, to calculate the degree of coincidence between the spectrum at each position of the chromatogram peak and the reference spectrum as fraction purity at each position of the chromatogram peak. The calculated fraction purity values are classified in colors, for example, and displayed on a display part. Thus, it is possible to readily decide whether the measured peak consists of a single component or at least two components, and which time range consists of a single component.

10 Claims, 6 Drawing Sheets

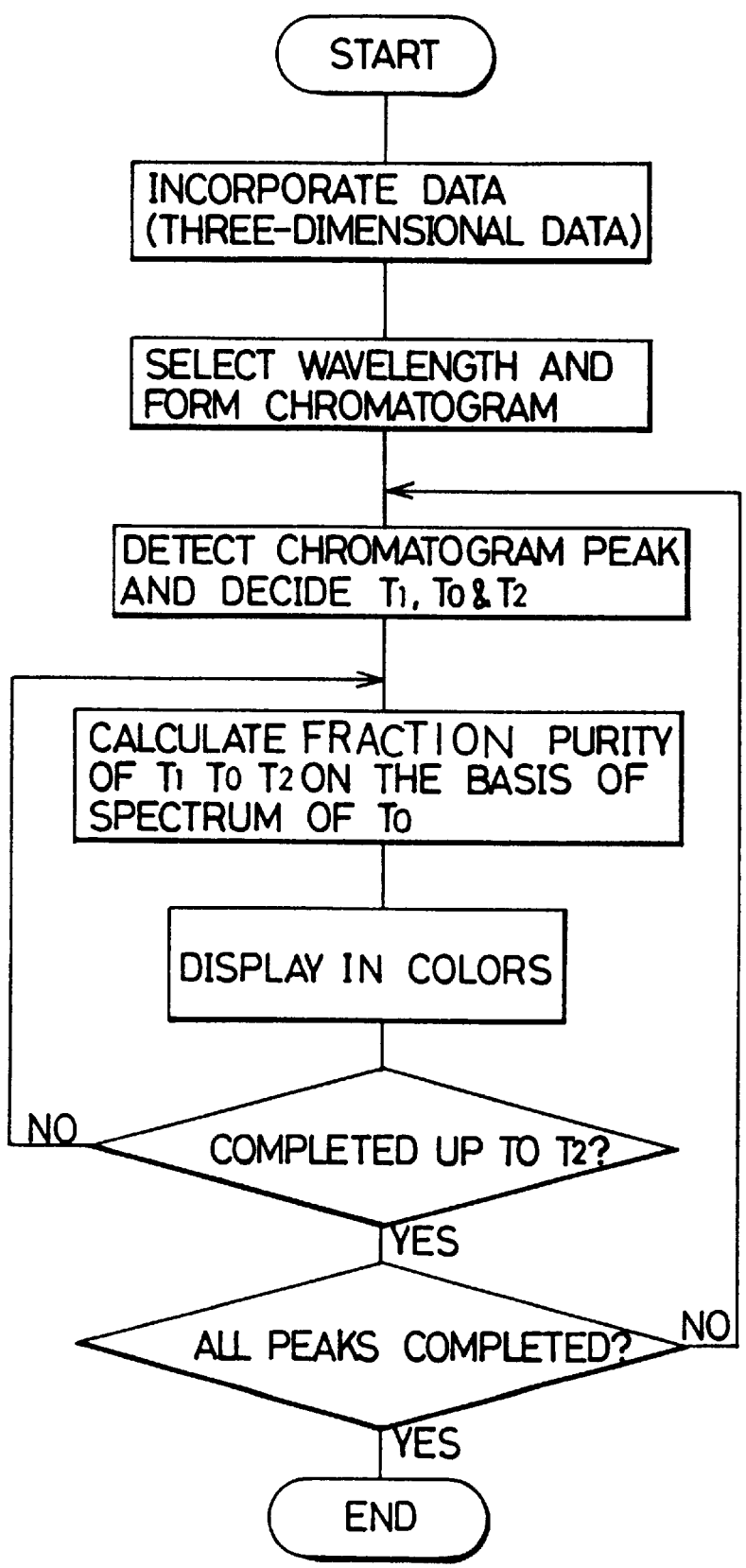

FRACTION PURITY MEASURING APPARATUS FOR CHROMATOGRAM PEAK

BACKGROUND OF THE INVENTION

1. Field of the Invention

The present invention relates to an apparatus for measuring fraction purity of a chromatogram peak in liquid chromatography or flow injection analysis.

The present invention also relates to a fraction collector for separating a sample into fractions with a liquid chromatograph thereby collecting designated fractions.

2. Description of the Background Art

In liquid chromatography or flow injection analysis, a chromatogram peak is obtained with time. Even if such a peak has a simple configuration, however, it may consist of at least two components in an inseparated state.

In order to decide whether or not a chromatogram peak as obtained consists of only a single component, employed is a specific chromatogram method, which is adapted to obtain chromatograms with two different wavelengths through an optical detector and take the ratio of the two chromatograms, thereby measuring fraction purity values of peaks. A peak which consists of a single component has a constant wavelength characteristic in every position. Therefore, the ratio of two chromatograms taken with different wavelengths remains constant in all positions. If the peaks consist of at least two components, on the other hand, wavelength characteristics of spectra are varied with positions of the peaks due to difference of component rates, whereby the ratio of the chromatograms is varied with the positions of the peaks.

When the fraction purity is measured by such a specific chromatogram method, it is possible to decide whether the as-obtained peak consists of a single component or at least two components. However, it is difficult to decide the percentage of such a possibility that the peak consists of a single component in a certain range between its start and end points. Therefore, it is difficult to decide time range for fraction collecting, for example, by the specific chromatogram method.

In order to collect fractions of a sample by liquid chromatography, employed is a method of previously setting collecting times for the target components in response to the retention times of the components, or a method of checking the order of the peaks of the target components on the chromatogram for collecting fractions appearing on the peaks of the order upon peak detection.

In the method responsive to the retention times, the fractions may be erroneously collected in positions displaced from the peaks of the target components since the retention time of each component is varied with slight difference of temperatures or mobile phases, or difference between injection volumes of the sample. In the method responsive to the peak order, on the other hand, the order may be upset by contamination of an unexpected impurity such that other components are erroneously collected. Thus, it is difficult to correctly collect fractions by the conventional method.

SUMMARY OF THE INVENTION

A first object of the present invention is to provide a fraction purity measuring apparatus, which can display fraction purity over a range of start to end points of a chromatogram peak so that it is possible to readily recognize time range suitable for fraction collecting.

A second object of the present invention is to provide a fraction collector which can reliably collect target components without depending on an index, such as retention times or a peak order, that may be varied with conditions.

FIG. 1 is a block diagram showing the inventive fraction purity measuring apparatus. This apparatus comprises a data storage part 2 for storing spectrum data received from a multi-wavelength detector or a mass spectrometer which is connected with a chromatograph, a chromatogram forming part 4 for forming a chromatogram from the data stored in the data storage part 2, a peak detecting part 6 for detecting the peak of the as-formed chromatogram, a fraction purity calculating part 8 for calculating the degree of coincidence between a reference spectrum and a spectrum in each position of the chromatogram peak thereby calculating fraction purity at each position of the peak, and a display part 10 for displaying the calculated fraction purity. The reference spectrum can be prepared from a known spectrum of a component to be identified, or a spectrum at a top of a peak to be identified. When a known spectrum is employed, a reference spectrum storage part is provided for storing the data thereof.

FIG. 2 (A) shows a peak of a chromatogram which is formed with reference to a certain wavelength from data obtained by measuring a spectrum per time instant in liquid chromatography or flow injection analysis. FIG. 2 (B) shows a spectrum So ($\lambda$) at a time To of a top of such a peak. FIG. 2 (B) also shows a spectrum S ($\lambda$) at a time of an arbitrary position T of the peak. On the basis of the spectrum So ($\lambda$), it is possible to obtain fraction purity at the arbitrary position T of the peak by calculating the degree of coincidence between the spectra So ($\lambda$) and S ($\lambda$). Such a degree of coincidence is expressed as follows, for example:

$$\text{Degree of Coincidence} = \frac{\sum_{i=1}^{n} So_i \cdot S_i}{\sqrt{\sum_{i=1}^{n} So_i^2 \cdot \sum_{i=1}^{n} S_i^2}}$$

where So ($\lambda$)=Soi (i=1, 2, . . . , n) and S ($\lambda$)=Si (i=1, 2, . . . , n).

Such a degree of coincidence can be colored every range to be displayed on a display unit, or can be displayed on a display unit or a printer as a numerical value, for example.

In the fraction collector according to the present invention, spectrum data of a component to be collected is stored and a liquid chromatograph effluent is analyzed to sample spectrum data of the effluent fraction for obtaining the degree of coincidence between the spectrum data of the effluent fraction and the aforementioned previously stored spectrum data. If the degree of coincidence is in excess of a constant value, a fraction representing the peak is collected.

A method of comparing spectra or mass spectra is employed for identifying substances. If the spectra of two substances are in excellent coincidence with each other, the substances can be regarded as the same type of substances. The inventive fraction collector is adapted to identify a chromatograph effluent fraction and a target substance by such spectrum comparison for collecting an effluent fraction which can be regarded as being of the same type as the target substance. Thus, it is possible to correctly collect target components regardless of displacement in retention time or appearance of an impurity peak.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a flow chart showing the operation of an embodiment of the present invention;

DESCRIPTION OF THE PREFERRED EMBODIMENTS

Figure 3:
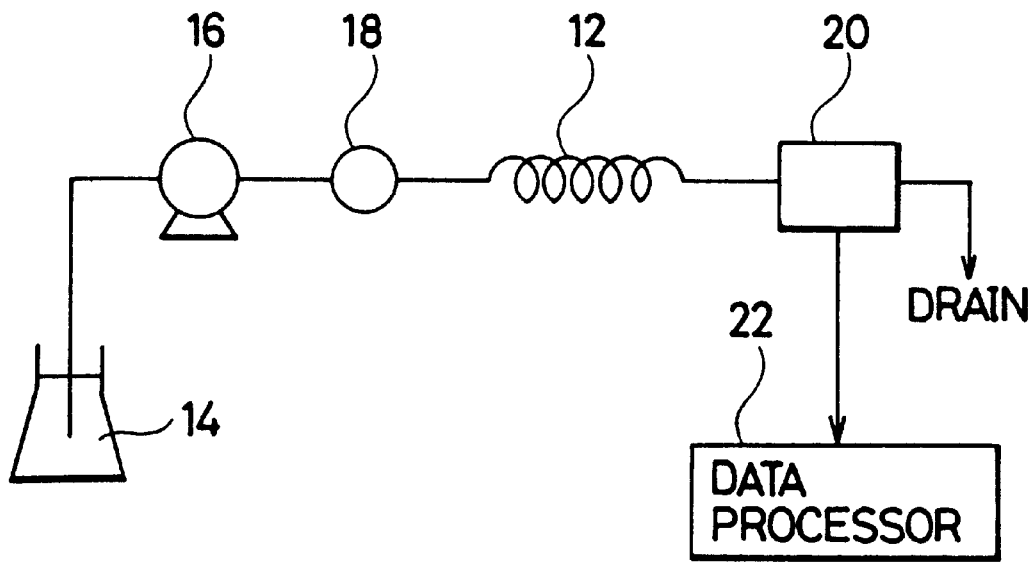
FIG. 3 is a passage diagram showing an exemplary liquid chromatograph to which the fraction purity measuring apparatus according to the present invention is applied.

FIG. 3 shows an exemplary liquid chromatograph to which a fraction purity measuring apparatus according to the present invention is applied.

This liquid chromatograph comprises a column 12, to which an eluant 14 is supplied through an eluant supply pump 16. A sample injection part 18 is provided between the eluant supply pump 16 and the column 12, so that an injected sample is fed to the column 12 with the eluant 14, to be separated in the column 12 and detected by a detector 20. An effluent from the detector 20 is discharged into a drain.

The detector 20 is formed by an optical detector, such as a spectrometer for ultraviolet and visible regions, for example, which can measure a chromatogram as well as measure a spectrum at each point of time. A detection signal outputted from the detector 20 is transmitted to a data processor 22, to be processed therein.

Figure 1:
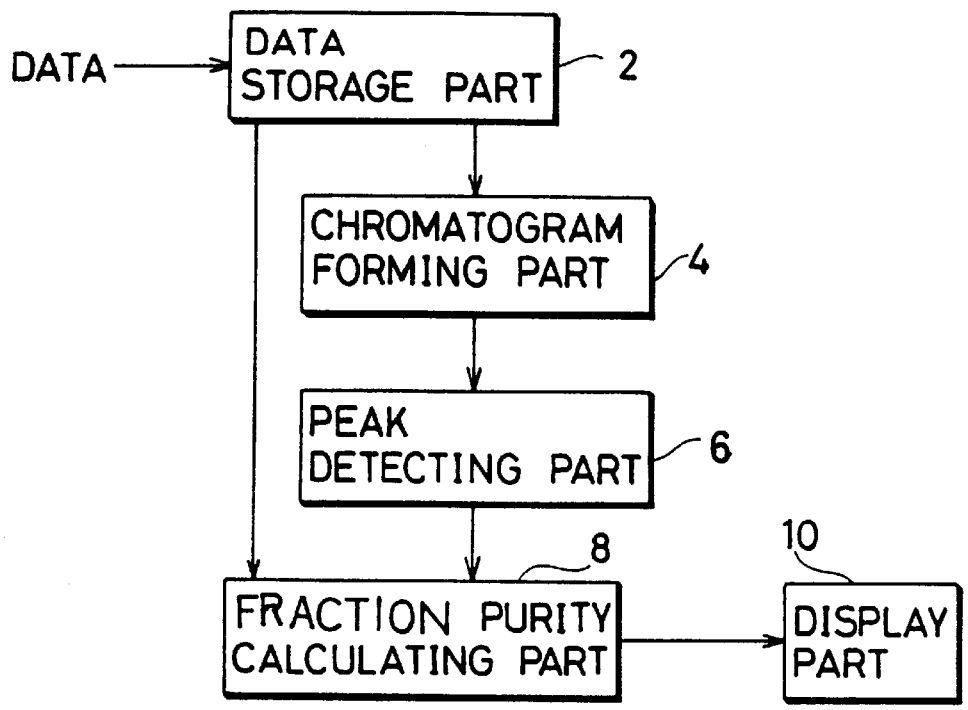
FIG. 1 is a block diagram showing a fraction purity measuring apparatus according to the present invention.
Figure 2:
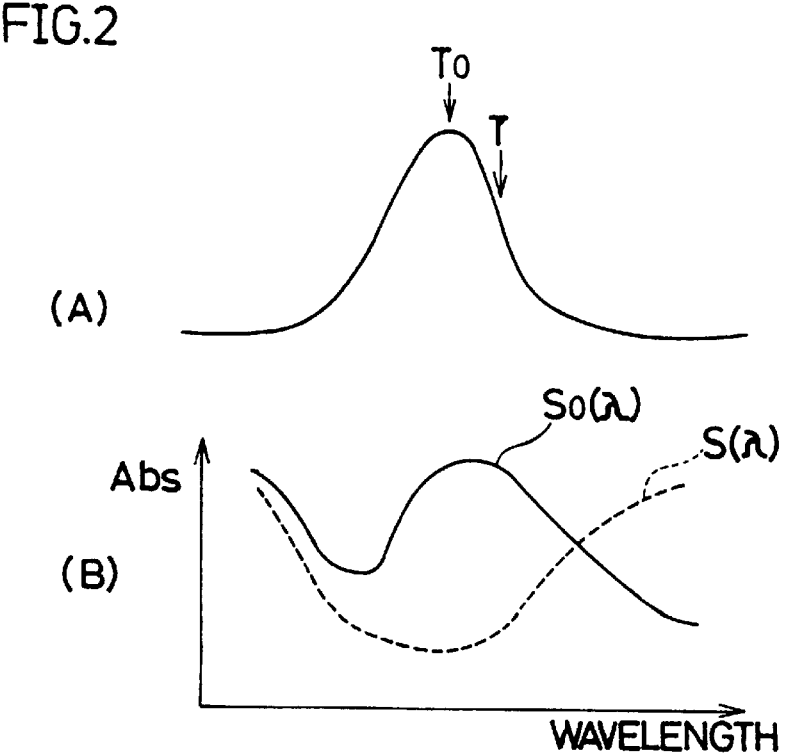
FIG. 2 (A) illustrates a chromatogram peak, and FIG. 2 (B) illustrates exemplary spectra of a top and another point of a peak.

The parts shown in FIG. 1 are realized by the data processor 22.

The operation of this embodiment is now described with reference to FIGS. 4 and 5.

Data from the detector 20 are incorporated and stored in the data storage part 2. The data are three-dimensional data indicating successive spectra of fractions which are separated in the column 2. A specific wavelength is selected from the stored data, to form a chromatogram from time variation of absorbance as to the wavelength. The chromatogram is displayed on a CRT etc. of the display part 10.

The peak of the as-formed chromatogram is detected, to obtain a start point T1, a top T0 and an end point T2 of this peak, whose fraction purity is to be obtained.

Figure 5:
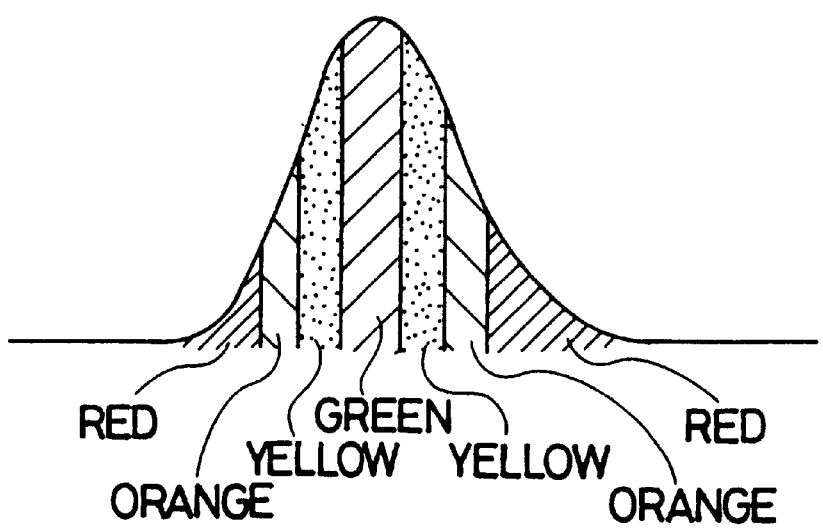
FIG. 5 illustrates exemplary color display of measured fraction purity values.

On the basis of the spectrum of the top T0, fraction purity values are calculated at respective points of time in the range between T1 an T2. The results of such calculation are classified in accordance with previously set purity levels, and expressed in colors along the range thereof, for example. The fraction purity values are classified as follows, for example:

0 to 0.5 . . . red
0.5 to 0.7 . . . orange
0.7 to 0.8 . . . yellow
0.8 to 1.0 . . . green This operation is performed from the start point T1 to the end point T2 of one peak, and the result is displayed on a display part such as a CRT in colors as shown in FIG. 5, for example.

The aforementioned operation is repeated as to every peak whose fraction purity is to be obtained.

While the fraction purity values are easily recognized when the same are displayed in colors as shown in FIG. 5, it is not requisite to display the same in colors. Alternatively, the fraction purity values may be plotted with respect to time, or displayed in numerical values.

According to the fraction purity measuring apparatus of the present invention, fraction purity values at respective points of a chromatogram peak are measured from the degree of coincidence between the reference spectrum at the top of the chromatogram peak and the spectrum of another position. Thus, it is possible to readily decide whether a measured peak consists of a single component or at least two components, as well as to decide which range consists of a single component. Consequently, it is possible to set a range for fraction collecting, for example, on the basis of the result of measurement of the fraction purity.

Figure 6:
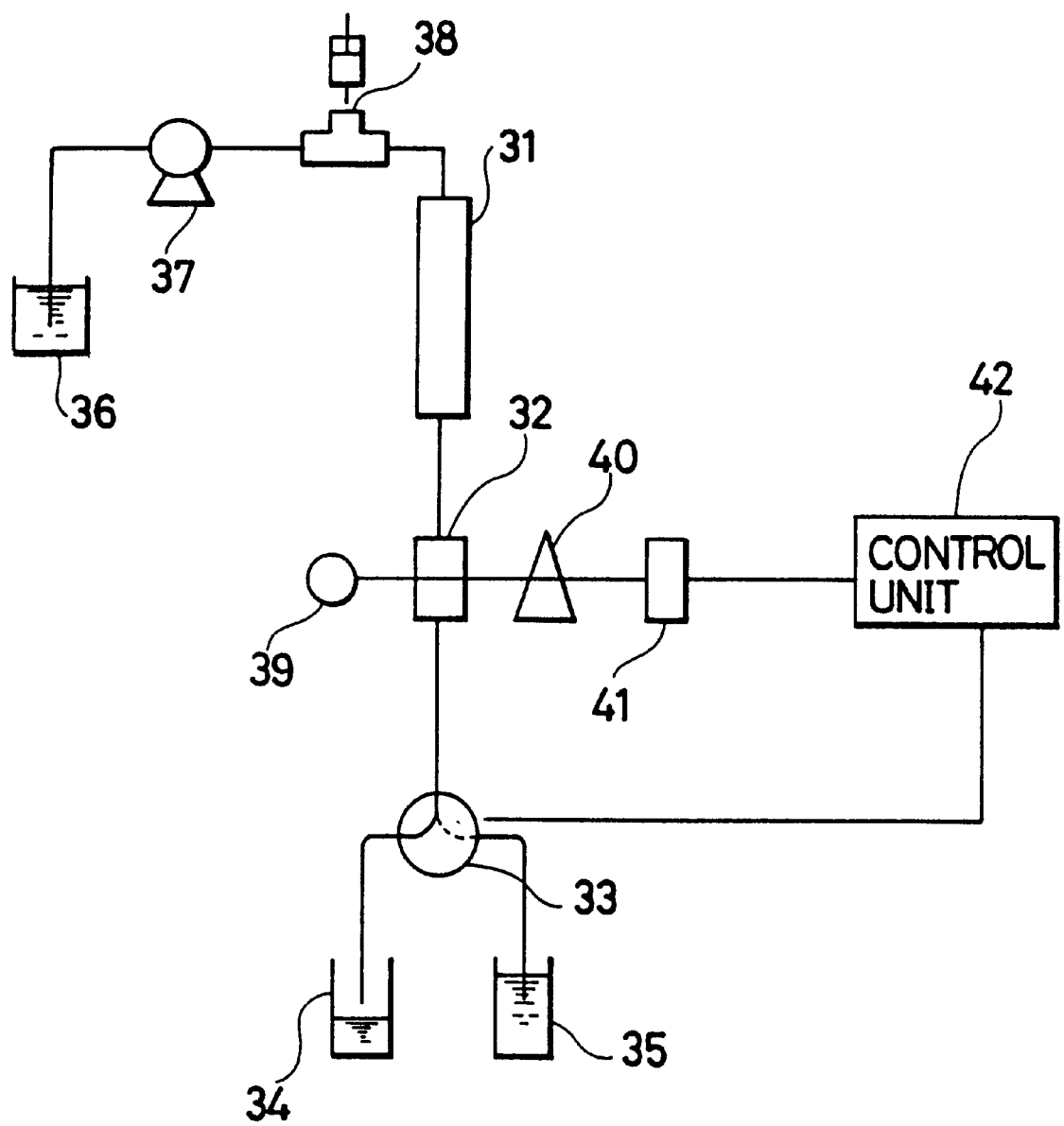
FIG. 6 is a passage diagram showing the overall structure of a fraction collector according to an embodiment of the present invention.

FIG. 6 shows an embodiment of a fraction collector according to the present invention. This apparatus comprises a liquid chromatograph column 31, a flow cell 32 which receives an effluent from the column 31, a fraction collecting cross valve 33, a fraction collecting vessel 34, a drainage receiver 35, a mobile phase liquid 36, a pump 37 for feeding the mobile phase liquid 36 to the column 31, and a sample injection part 38. This apparatus further comprises a light source 39, a spectroscope 40 which is arranged facing the light source 39 with the flow cell 32 between, and a photodiode array 41 which is arranged on a spectrum image surface formed in the spectroscope 40. The light source 39, the spectroscope 40 and the photodiode array 41 form a multiwavelength spectrometer. A control unit 42, which incorporates an output signal from the photodiode array 41, performs data processing and controls the cross valve 33.

Figure 7:
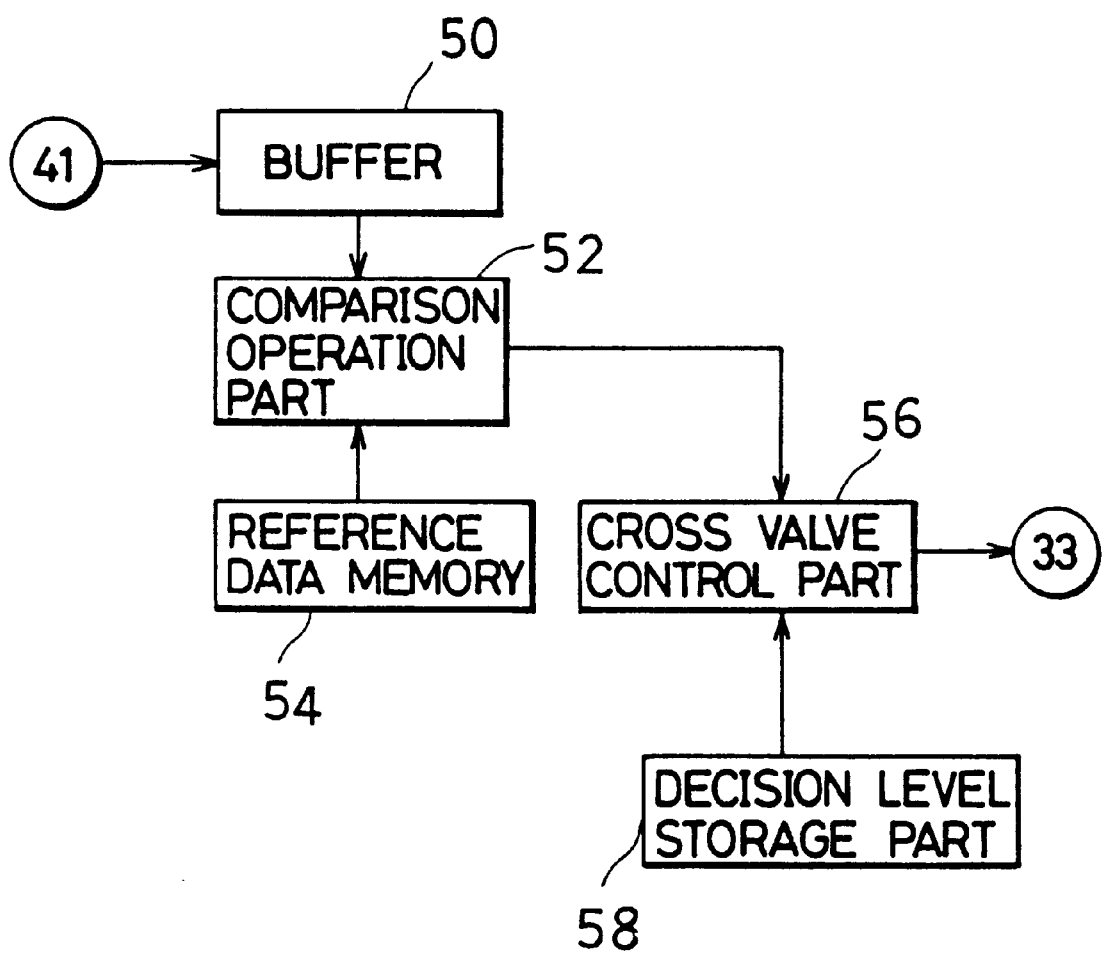
FIG. 7 is a functional block diagram showing a control unit of the embodiment shown in FIG. 6.

As shown in FIG. 7, the control unit 42 has functional parts including a buffer memory 50 for temporarily storing output data from the photodiode array 41, a reference data memory 54 for storing spectrum data of components to be collected, a comparison operation part 52, a decision level storage part 58, and a cross valve control part 56 for comparing an output from the comparison operation part 52 with a decision level for switching the cross valve 33 toward the fraction collecting vessel 34 when the output from the comparison operation part 52 is in excess of the decision level while switching the cross valve 33 toward the drainage receiver 35 in other case.

Figure 8:
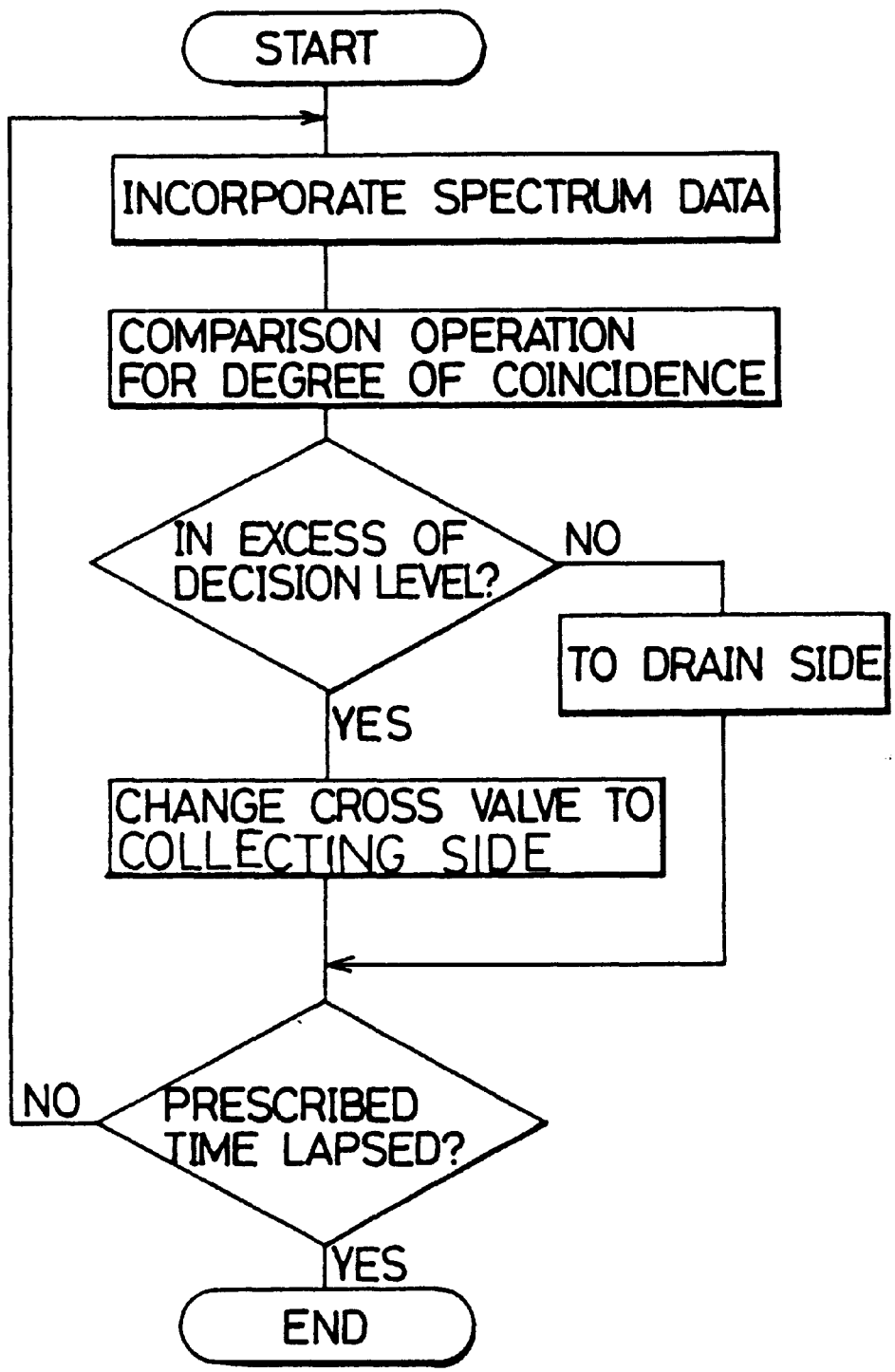
FIG. 8 is a flow chart showing the operation of the control unit of the embodiment shown in FIG. 6.

FIG. 8 is a flow chart showing the operation of the aforementioned control unit 42. The column 31 is supplied with the mobile phase liquid, so that the operation is started after a sample is injected into the sample injection part 38. Spectrum data is inputted from the photodiode array 41 into the buffer memory 50. As understood from FIG. 6, the spectrum data is related to the absorption spectrum of the column effluent. Then, the spectrum data is subjected to comparison operation with absorption spectrum data of a target component which is stored in the reference data memory 54, and a decision is made as to whether or not the calculated degree of coincidence is greater than a decision level stored in the decision level storage part 58. If the decision is of YES, the cross valve 33 is switched toward the fraction collecting vessel 34, while the cross valve 33 is switched toward the drainage receiver 35 if the decision is of NO. This operation is continued for a constant period of time, and terminated after a lapse of this period. Such a constant period is so set that the injected sample entirely flows out to enable injection of a next sample for the column 31.

Exemplary comparison operation for the spectrum of a column effluent fraction and that of a target component is now described. Spectrum data are formed by photometric outputs at several wavelengths $\lambda 1, \lambda 2, \ldots \lambda n$. A set of n such values can be regarded as a single vector. Assuming that S represents the vector of the spectrum data of the column effluent fraction and U represents that of the spectrum data of the target component, the spectrum data of these components are coincident with each other when the vectors are parallel to each other, and the lengths of the vectors merely represent a ratio of concentration. Since the column effluent fraction is a solution of a mobile phase solution in practice and the spectrum thereof is overlapped with the spectrum of the mobile phase, the spectrum of the column effluent fraction rarely completely coincides with the reference spectrum of the target component. Thus, the components are regarded as being identical to each other when the spectrum vectors thereof are approximately parallel to each other to some extent. The degree of coincidence is operated by calculating the degree of parallelization between the two vectors. When the two vectors are parallel to each other, the scalar product for each value is 1 as to a standarized vector having a component value obtained by dividing the vector component by the length of the vector. When such scalar products are in excess of a certain decision level which is approximate to 1, therefore, the components are decided as being identical to each other. Assuming that Si (i=1, 2, ..., n) represents each component of the vector S of the spectrum of the column effluent fraction and Soi represents each component of the vector So of the spectrum of the target component, the components of the respective standarized vectors are:

$$(Si) = Si \Big/ \sqrt{\sum_{i=1}^{n} Si^2}$$

for the column effluent fraction, and $$(Soi) = Soi \Big/ \sqrt{\sum_{i=1}^{n} Soi^2}$$

for the target component.

The condition for parallelization is expressed as:

$$\sum_{i=1}^{n} (Si) \cdot (Soi) = 1$$

As to Si and Soi, the above is expressed as follows:

$$\frac{\sum_{i=1}^{n} (Si) \cdot (Soi)}{\sqrt{\sum_{i=1}^{n} (Si)^2 \cdot \sum_{i=1}^{n} (Soi)^2}}$$

According to the fraction collector of the present invention, the target component can be correctly collected even if the retention time, the peak order etc. of the fraction to be collected are varied, whereby it is possible to improve reliability of a fraction collecting operation.

Although the degree of coincidence is decided with reference to spectrum data in the aforementioned embodiment, such decision may alternatively be made with reference to mass spectrum data.

Although the present invention has been described and illustrated in detail, it is clearly understood that the same is by way of illustration and example only and is not to be taken by way of limitation, the spirit and scope of the present invention being limited only by the terms of the appended claims.

The features disclosed in the foregoing description, in the claims and/or in the accompanying drawings may, both, separately and in any combination thereof, be material for realizing the invention in diverse forms thereof.

What is claimed is:

1. A chromatography apparatus, comprising:

an eluent supply;

a sample injection part for receiving sample;

a column connected to said eluent supply and said sample injection part;

a detector for generating a sample detection signal;

a data storage part for storing data from the sample detection signal from said detector;

a chromatogram forming part for forming a chromatogram spectrum from said data stored in said data storage part;

a peak detecting part for detecting a chromatogram peak of said chromatogram;

a fraction purity calculating part for calculating the degree of coincidence between a spectrum at an upper portion of said chromatogram peak and the chromatogram spectrum at each position of said chromatogram peak for calculating fraction purity at each position of said chromatogram peak; and a display part for displaying calculated fraction purity.

2. A fraction purity measuring apparatus in accordance with claim 1, wherein said detector is an optical multi-wavelength detector.

3. A fraction purity measuring apparatus in accordance with claim 1, wherein said detector is a mass spectrometer.

4. A chromatography apparatus in accordance with claim 1, wherein the degree of coincidence is calculated by the following expression:

$$\text{Degree of Coincidence} = \frac{\sum_{i=1}^{n} Soi \cdot Si}{\sqrt{\sum_{i=1}^{n} Soi^2 \cdot \sum_{i=1}^{n} Si^2}}$$

where Soi (i=1, 2, . . . , n) represents said reference spectrum and Si (i=1, 2, . . . , n) represents a spectrum in an arbitrary position of said peak.

5. A chromatography apparatus in accordance with claim 1, wherein said peak is classified in response to ranges of the degree of coincidence and displayed in colors based on the decree of coincidence.

6. A fraction purity measuring apparatus in accordance with claim 1, wherein the degree of coincidence at each position of said peak is displayed in a numerical value.

7. A chromatography apparatus in accordance with claim 1, including
switching means for guiding liquid chromatograph effluent to a fraction collecting vessel when said degree of coincidence is in excess of a prescribed value.

8. A chromotography apparatus in accordance with claim 7, wherein said detector is an optical multiwavelength detector.

9. A chromotography apparatus in accordance with claim 7, wherein said detector is a mass spectrometer.

10. A chromatography apparatus in accordance with claim 7, wherein the degree of coincidence is calculated by the following expression:

$$\text{Degree of Coincidence} = \frac{\sum_{i=1}^{n} Soi \cdot Si}{\sqrt{\sum_{i=1}^{n} Soi^2 \cdot \sum_{i=1}^{n} Si^2}}$$

where Soi (i=1, 2, . . . , n) represents said spectrum at an upper portion of said peak spectrum and Si (i=1, 2, . . . , n) represents a spectrum at an arbitrary position of said peak.

* * * * *